US006078840A

United States Patent [19]
Stokes

[11] Patent Number: 6,078,840
[45] Date of Patent: Jun. 20, 2000

[54] MEDICAL ELECTRICAL LEAD HAVING IMPROVED FIXATION

[75] Inventor: Kenneth B. Stokes, Anoka, Minn.

[73] Assignee: Medtronic, Inc., Minneapolis, Minn.

[21] Appl. No.: 09/149,019

[22] Filed: Sep. 8, 1998

Related U.S. Application Data

[63] Continuation of application No. 08/841,711, Apr. 30, 1997, abandoned.

[51] Int. Cl.$^7$ .......................................................... A61N 1/05
[52] U.S. Cl. .......................... 607/127; 607/126; 600/375
[58] Field of Search ................................... 607/127, 126, 607/122, 116, 119, 131; 600/375, 376–378, 374, 373, 372

[56] References Cited

U.S. PATENT DOCUMENTS

| 5,002,067 | 3/1991 | Berthelsen et al. ...................... 128/786 |
| 5,011,494 | 4/1991 | von Recum et al. ...................... 623/11 |
| 5,318,572 | 6/1994 | Helland et al. .......................... 607/121 |

OTHER PUBLICATIONS

"Quantitative Analysis of Fibroblast Morphology on Microgrooved Surfaces with Various Groove and Ridge Dimensions" — E.T. den Braber et al. (Biomaterials 1996, vol. 17 No. 21, pp. 2037–2044).
"Effect of Parallel Surface Microgrooves and Surface Energy on Cell Growth" — E.T. den Braber et al. (Journal of Biomedical Materials Research, vol. 29, 1995, pp. 511–518).
"Soft Tissue Response to Different Types of Sintered Metail Fibre–web Materials" — J.A. Jansen et al. (Biomaterials 1992, vol. 13, No. 13, pp. 959–968).
"Quantitative Analysis of Cell Proliferation and Orientation on Substrate with Uniform Parallel Surface Micro–grooves" — E.T. den Braber et al. (Biomaterials 1996, vol. 17, No. 11, pp. 1093–1099).
"Fibroblast Anchorage to Microtextured Surfaces" — J. Meyle et al. (Journal of Biomedical Materials Research, vol. 27, 1993, pp. 1553–1557).

*Primary Examiner*—Kennedy J. Schaetzle
*Attorney, Agent, or Firm*—Harold Patton; Thomas F. Woods; Michael J. Jaro

[57] ABSTRACT

The present invention is directed to a medical electrical lead having active fixation which features an improved fixation helix. In particular the present invention is a medical electrical lead having a fixation helix which features microgrooves. The microgrooves are dimensioned so as to minimize the foreign body response of the tissue into which the helix is implanted. The microgrooves preferably consist of a series of grooves parallel to the longitudinal axis of the helix, each groove has a depth of between approximately 0.1 to 30 microns, preferably between approximately 0.1 and 3, with 1 micron preferred; a width of between approximately 0.1 to 30 microns, preferably between approximately 0.1 and 3, with 1 micron preferred; and is spaced apart from every other groove by a distance of between approximately 0.1 to 30 microns, preferably between approximately 0.1 and 3, with 1 micron preferred. Although shown as square, the grooves may be of any shape, including rectangular, polygonal, rounded or even irregularly shaped.

21 Claims, 5 Drawing Sheets

MEDICAL ELECTRICAL LEAD HAVING IMPROVED FIXATION

This is a continuation of application Ser. No. 08/841,711 filed on Apr. 30, 1997 now abandoned.

FIELD OF THE INVENTION

This invention relates generally to the field of implantable medical devices, and more particularly to a medical electrical lead featuring an improved fixation mechanism which provides improved electrical performance.

BACKGROUND OF THE INVENTION

Various types of implantable leads are known and used. Cardiac pulse generators, in particular, use implantable leads to both sense cardiac function and deliver stimulation pulses. One type of commonly used implantable lead is an endocardial lead.

Endocardial leads are attached at their proximal end to an implantable pulse generator and at their distal end to the endocardium (or even myocardium) of a cardiac chamber. Often the lead assembly is inserted into the heart through a vein. The lead generally has an inner conductor covered by an insulative sheath.

The distal end of an endocardial lead may electrically couple with the endocardium by either an active fixation mechanism or a passive fixation mechanism. Passive fixation mechanisms, such as a tine assembly, lodge or passively fix the lead to the heart. Active fixation mechanisms use a structure, such as a helix or hook, to engage into or actively fix themselves to the heart, and in particular, to the myocardium.

A sharpened helix has been found to provide a reasonably secure means for actively fixing a lead to the heart. One drawback to the use of a helix is the tissue reaction between the heart tissue and the rigid helix. Specifically, the implantation of the helix within the heart tissue triggers the foreign body response. That is, the body launches a series of attacks and processes upon the helix, intending to either destroy the helix or at least encapsulate it within a protective capsule of tissue. The most visible evidence of this foreign body response is the layer of activated macrophages and collagen capsule around the helical coil. Such tissues detrimentally affect the electrical performance of the surrounding tissue and thus the ability of the lead contacting that tissue to either electrically stimulate and sense the tissue. As a result, if the helix itself is used as the electrode, or even if the electrode is near the helix, the stimulation thresholds may rise, typically as a function of time after implant.

In particular, maintaining a low stimulation threshold for an implantable medical device is important. Implantable pulse generators are battery-powered and thus have a finite operating life. Over time, the battery will deplete and ultimately the implanted pulse generator must be replaced. Replacement, however, involves a surgical procedure and should be avoided, if possible. Therefore, it is important to minimize the electrical current drain on the battery. A lead which minimizes such drain by maintaining low stimulation thresholds is desired. One approach to maintain low stimulation thresholds is to prevent or control the build-up of tissues such as collagen around the fixation mechanism.

SUMMARY OF THE INVENTION

The present invention is directed to a medical electrical lead having active fixation which features an improved fixation helix. In particular the present invention is a medical electrical lead having a fixation helix which features microgrooves. The microgrooves are dimensioned so as to minimize the foreign body response of the tissue into which the helix is implanted. The microgrooves preferably consist of a series of grooves parallel to the longitudinal axis of the helix, each groove has a depth of between approximately 0.1 to 30 microns, preferably between approximately 0.1 and 3, with 1 micron preferred; a width of between approximately 0.1 to 30 microns, preferably between approximately 0.1 and 3, with 1 micron preferred; and is spaced apart from every other groove by a distance of between approximately 0.1 to 30 microns, preferably between approximately 0.1 and 3, with 1 micron preferred. Although shown as square, the grooves may be of any shape, including rectangular, polygonal, rounded or even irregularly shaped.

The drawings are not necessarily to scale.

DETAILED DESCRIPTION OF THE PRESENT INVENTION

The present invention is not limited to only atrial or ventricular pacing leads, and may be employed in many of various types of therapeutic or diagnostic devices including nerve, muscle or defibrillation leads. It is to be further understood, moreover, the present invention may be employed in many of various types of therapeutic or diagnostic catheters and is not limited only to the fixing of electrical leads. For purposes of illustration only, however, the present invention is below described in the context of endocardial pacing leads.

Figure 1:
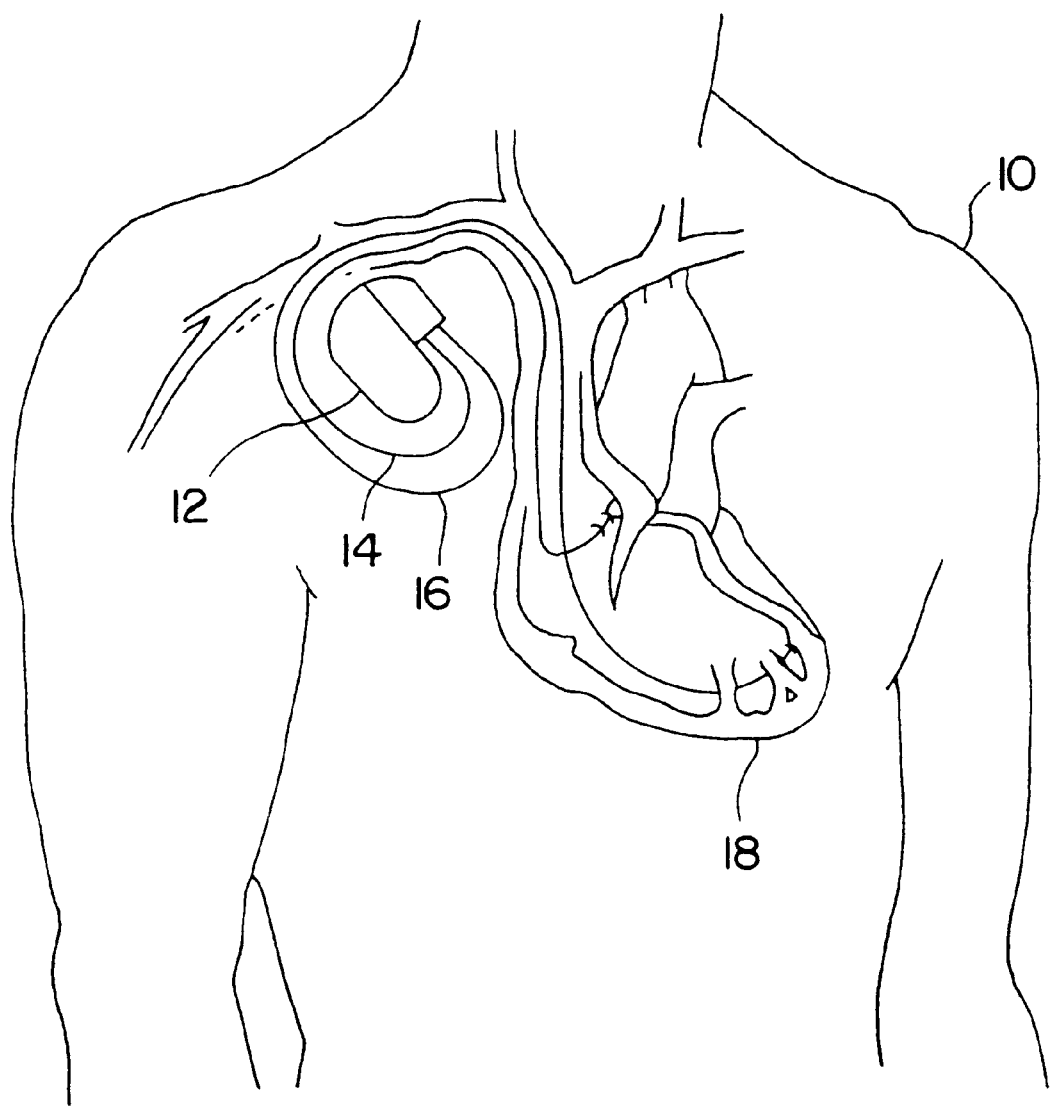
FIG. 1 depicts the venous positioning and placement of transvenous endocardial leads in a patient.

FIG. 1 depicts a typical arrangement of a pacing system implanted in a patient 10, the pacing system comprising a subcutaneously disposed pacemaker 12 and transvenous endocardial pacing leads 14 and 16. In FIG. 1, the distal end of pacing lead 14 is shown disposed generally in the atrial region of the patient's heart 18, while the distal end of pacing lead 16 is disposed generally in the ventricular region of heart 18.

Figure 2:
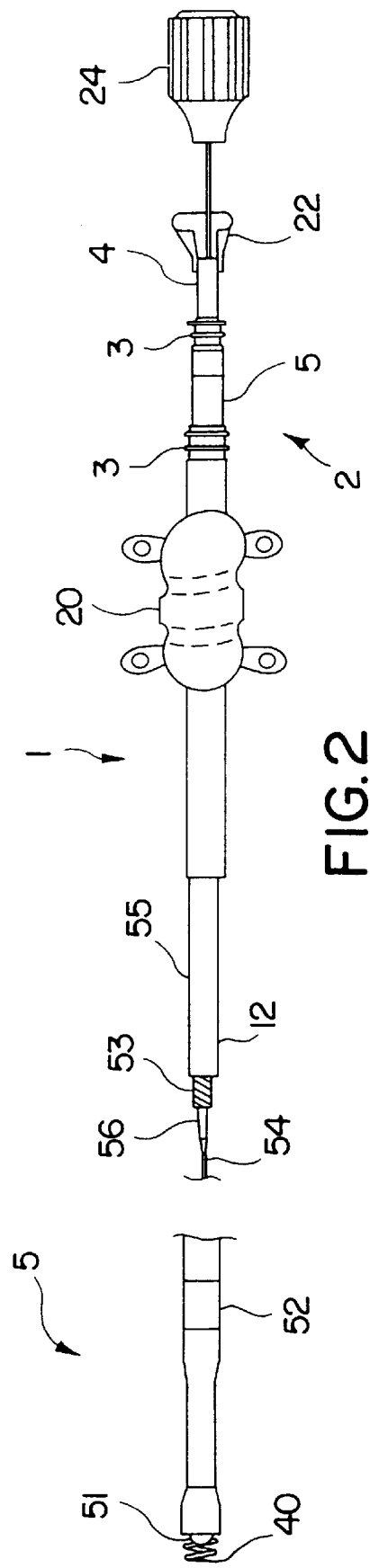
FIG. 2 depicts a body-implantable, endocardial fixed screw lead according to the present invention.

FIG. 2 depicts in general the configuration of lead 1. As seen lead 1 has connector assembly 2 at proximal end for coupling lead 1 to an implantable pulse generator (not shown in this FIG.) Connector assembly 2 preferably has sealing rings 3, terminal pin 4 and terminal ring 5 all of a type known in the art. Of course, other types of connector assemblies may be used, such as simple pins or even stripped or exposed wire.

An anchoring sleeve 20 (shown partially in cross-section) may also be provided for suturing lead 1 to body tissue. Anchoring sleeve 20 and connector assembly 2 are preferably fabricated from silicone rubber, although they may also be constructed of any other suitable biocompatible material known in the art, such as polyurethane.

Lead 1 may also include stylet guide 22 (shown in partial cut-away) and stylet assembly 24 coupled to connector assembly 2 for imparting stiffness to lead 1 during placement> In some designs the stylet may be used for actuation of the lead's fixation mechanism 40, described below. Stylet guide 22 and stylet assembly 24 are typically discarded after use and before connection of terminal pin 4 to a pulse generator.

Electrode 50 and fixation assembly 40 are disposed at distal end of lead 1. Electrode, as shown, is bipolar consisting of tip electrode 51 and ring electrode 52. As will be appreciated by those of ordinary skill in the art, tip electrode 51 and ring electrode 35 are coupled to separate, insulated lead conductors which extend along the length of lead body 12. Of course, other electrode configurations may also be used with the present invention, including unipolar or even multipolar designs Tip electrode 51 used in the lead shown in FIG. 2 is preferably fashioned using a porous spherical platinum composition coated with platinum black. The porosity, together with the platinum black coating is intended to reduce the foreign body response, stimulation thresholds and signal source impedance and polarization. Although platinum is the preferred other materials may also be used, including but not limited to such materials as palladium, titanium, tantalum, rhodium, iridium, carbon, vitreous carbon and alloys, oxides and nitrides of such metals or other conductive or even semi-conductive materials. Of course, some materials are incompatible with others and may not be effectively used together. The limitations of specific materials for use with others is well known in the art. Examples of acceptable electrode materials and associated fabrication techniques employed to achieve the micro-porous structure may be found in Stokes, U.S. Pat. No. 4,506,680 and related Medtronic U.S. Pat. Nos. 4,577,642; 4,606,118 and 4,711,251 and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, each of which is herein incorporated by reference.

Although not shown in FIG. 2, lead 1 preferably includes a monolithic controlled release device (MCRD) preferably constructed from silicone rubber to elute an anti-inflammatory agent proximate electrode 51. The anti-inflammatory agent, preferably a derivative of dexamethasone, such as the steroid dexamethasone sodium phosphate, is loaded in the MCRD. The steroid also is deposited within electrode 51 material by application of a solution of dexamethasone sodium phosphate dissolved in a mixture of isopropanol and distilled or deionized water. Anti-inflammatory agents or other therapeutic agents may further be positioned with the micro grooves of the helix discussed below. Such agents may or may not be soluble in water, and may include the anti-inflammatory agent beclomethasone, dexamethasone acetate or dexamethasone sodium phosphate.

Lead body 12 has concentric multi-filar conductor coils 53, 54 of a suitable alloy, such as MP35N located between concentric insulative sheaths 55, 56 made of silicone rubber, polyurethane, or the like. This configuration allows for coils 53, 54 to be insulated throughout their respective lengths. Coil 53 is electrically coupled with ring electrode 52, while coil 54 is electrically coupled with tip electrode 51. A lumen exists along the length of lead body 12, such that a stylet may be received therein. Fixation mechanism 40 is preferably constructed of an biocompatible conductor, such as a platinum-iridium alloy.

Figure 3:
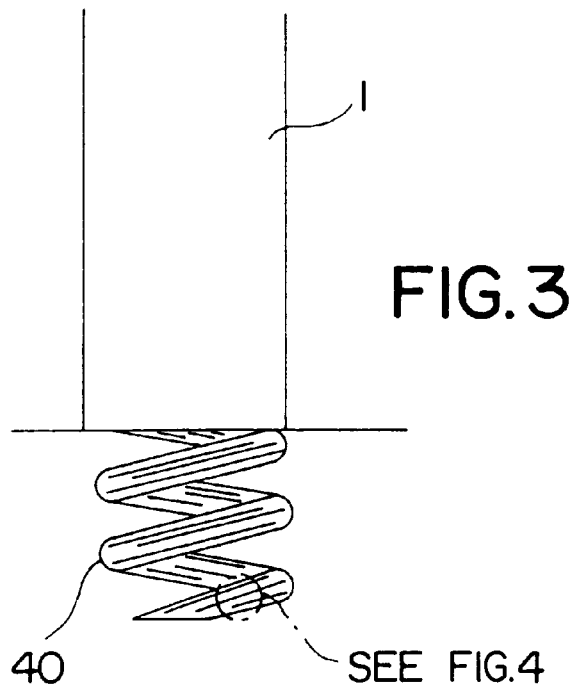
FIG. 3 shows a detailed view of the helix.

Turning now to FIG. 3 which shows a detailed view of the helix. As seen helix 40 has a series of longitudinal grooves 90 on the outer surface. Grooves 90 are better viewed in FIG. 4, which shows a detailed view of the surface of the helix shown in FIG. 3. As seen grooves 90 are parallel to each other. Each groove, moreover, continues in as a single uninterrupted groove along the entire outer surface of the helix, from the base of the helix at the lead body to the tip of the helix. Of course, other groove orientations may also be used, such as non-parallel or various interrupted grooves. For example, groove may be helical about the helix itself or may even consist of a series of concentric rings about the helix.

Figure 4:
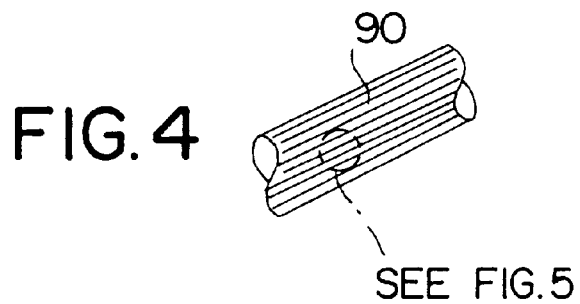
FIG. 4 shows a detailed view of the surface of the helix shown in FIG. 3.
Figure 5:
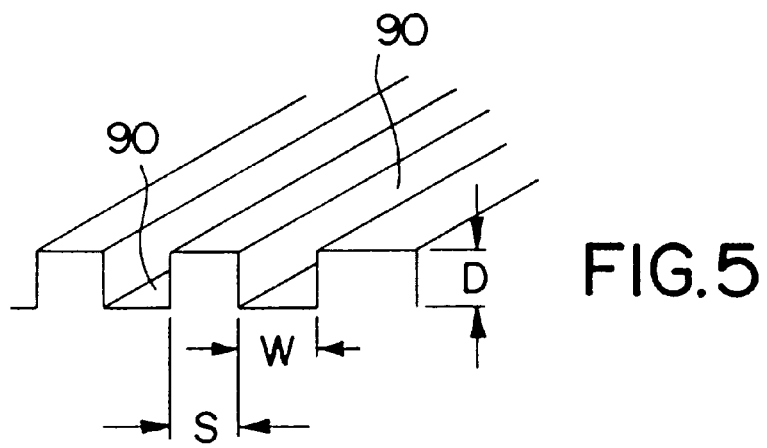
FIG. 5 shows a detailed view of the surface of the helix shown in FIG. 4, and in particular, a detailed view of the grooves along the helix.

FIG. 5 shows a detailed view of the surface of the helix shown in FIG. 4, and in particular, a detailed view of the grooves 90 along the helix. As seen each groove 90 is a square groove having sides which meet at ninety degree angles and has a depth "D" of between approximately 0.1 to 30 microns, preferably between approximately 0.1 and 3, with 1 micron preferred; a width "W" of between approximately 0.1 to 30 microns, preferably between approximately 0.1 and 3, with 1 micron preferred; and is spaced apart from every other groove by a distance "S" of between approximately 0.1 to 30 microns, preferably between approximately 0.1 and 3, with 1 micron preferred. Although shown as square, grooves may be of any shape, including rectangular, polygonal, rounded or even irregularly shaped. What is important is the dimension of the grooves are such that they are suitably sized to permit atraumatic insertion through the myocardium while also optimizing healing due to minimal activation of the macrophages. In addition, if the helix used extends and retracts, then the present invention provides for all of these advantages while also permitting the helix to readily move through any seals at the distal end (discussed in some detail below.)

Figure 6A:
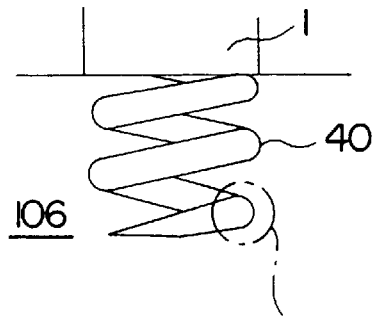
FIG. 6 depicts the foreign body response, including the buildup of collagen, in the area near a prior art fixation helix.
Figure 6B:
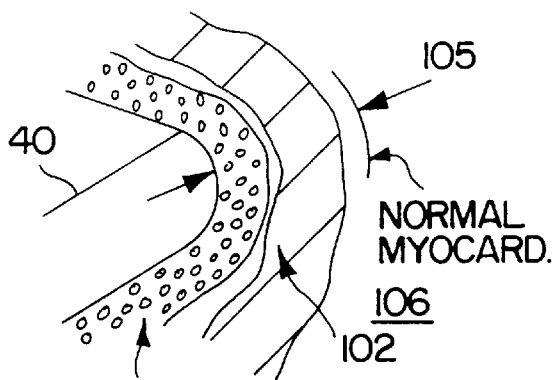

FIG. 6 depicts the foreign body response, including the buildup of collagen, in the area near a prior art fixation helix. As seen adjacent helix 40 lies a layer of activated macrophages 100. Positioned adjacent macrophages 100 is a layer of a collagen capsule 102. As seen collagen capsule has a series of stringers extending therefrom and into disarranged myocardium 104. Finally, positioned at a distance 105 away from the helix is normal myocardium 106.

Figure 7A:
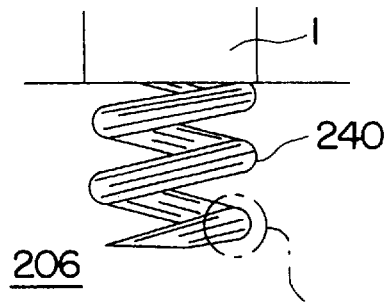
FIG. 7 depicts the decreased foreign body response in the area near a fixation helix according to the present invention.
Figure 7B:
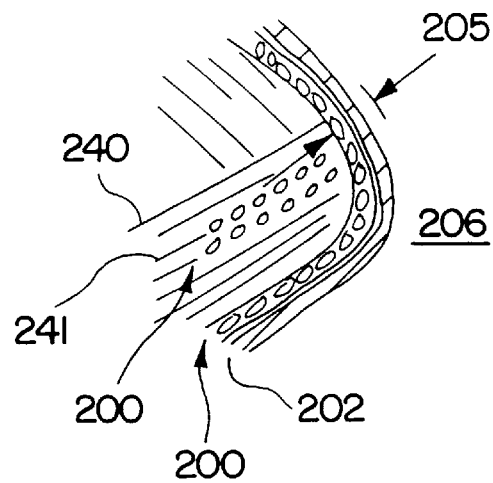

FIG. 7 depicts the decreased foreign body response in the area near a fixation helix according to the present invention. As seen, helix 240 has a series of microgrooves 241. A layer of activated macrophages 200 lies adjacent and even within grooves. Positioned adjacent macrophages is a layer of a collagen capsule 202. As seen collagen capsule has a series of stringers extending therefrom and into disarranged myocardium 204. Finally, positioned at a distance 205 away from the helix is normal myocardium 206. As can be appreciated by comparing this FIG. 7 with FIG. 6, the distance normal myocardium is from helix is much less with a helix featuring microgrooves according to the present invention as compared to a helix of the prior art (FIG. 6.)

Figure 8:
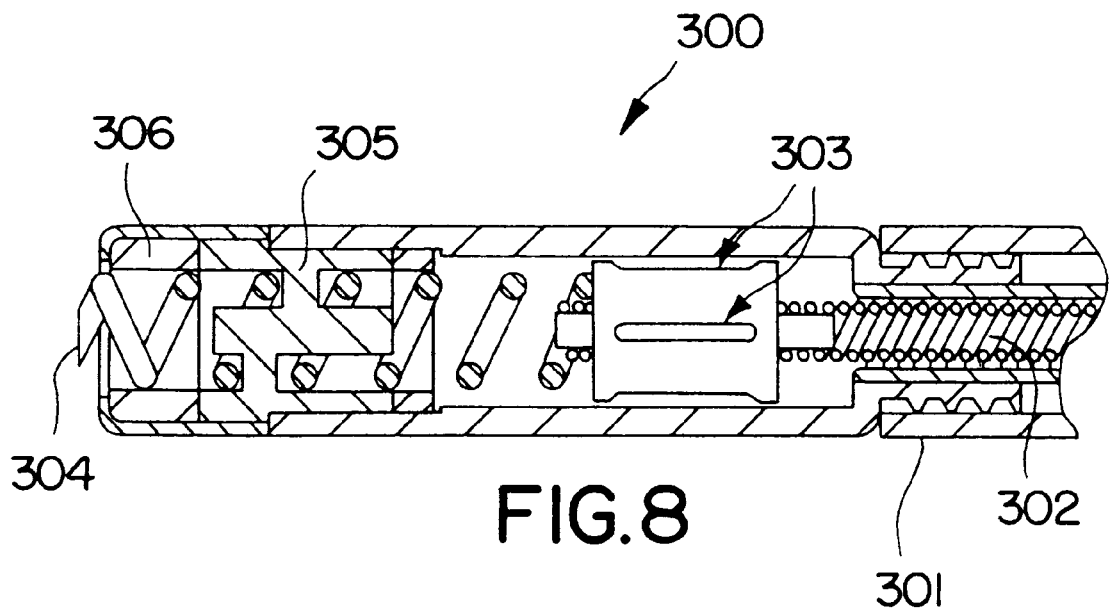
FIG. 8 is a sectional view of an alternate embodiment of the present invention.

FIG. 8 is a sectional view of the distal end of an alternative embodiment of the present invention. In particular, as discussed above, in this embodiment the helix extends and retracts from the distal end of the lead body. Such helix movement is well known in the pacing art and may be found, for example, in the Medtronic 4068 medical electrical lead. As seen, lead 300 has a lead body 301 of an insulative sheath with a coiled conductor 302 positioned therein. Conductor is mechanically and electrically joined to crimp core 303 which, in turn, is further joined to helix 304 which extends through seal assembly 305. Through such a configuration, rotation of the crimp core causes the helix to either extend or retract from the distal end of the lead through seal 305. Seal is provided to prevent the ingress of body fluids into the pacing lead which may thereby affect electrical performance. Also positioned at the distal end of the lead adjacent to the helix is an MCRD to elute anti-inflammatory agents or other therapeutic agents as discussed above.

Figure 9:
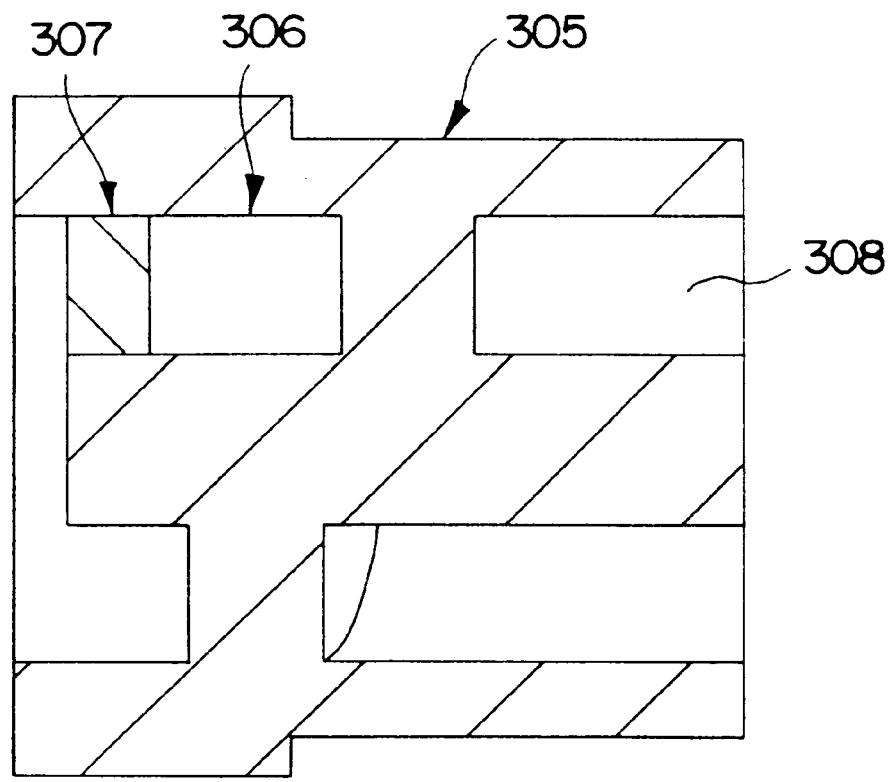
FIG. 9 is a sectional view of a seal used in the embodiment shown in FIG. 8.

FIG. 9 depicts a detailed sectional view of seal 305. As seen in this view, seal has an annular cavity 308 into which the helix runs through. The annular cavity terminates at its distal end where the seal runs through a layer of material. In particular, at this point the helix runs through a plug of medical adhesive 306 as well as urethane 307. Through this construction the seal prevents the ingress of bodily fluids into the interior portion of the lead while still permitting the helix to be retracted from the distal end of the lead through the seal. As discussed above, the groove design of the present invention permits the helix to extend through these various layers while maintaining the seal, i.e. preventing the ingress of bodily fluids. It should be understood, however, the present invention is not merely limited to only having grooves at the exterior of the helix in this embodiment but may also include the surface treatment such that the lubricity of a grooved helix through the seal is increased.

While the invention has been described in the context of the fixing of endocardial pacing leads, the present invention is not limited to only endocardial leads, but may also be used within a myocardial or epicardial lead. Indeed, the present invention is not limited to only fix cardiac pacing leads, and may be employed in fixing many of various types of therapeutic or diagnostic devices including nerve, muscle or defibrillation leads. It is to be further understood, moreover, the present invention may be employed in many of various types of therapeutic or diagnostic catheters and is not limited only to the fixing of only electrical leads. Moreover, the present invention may be used in an device in which the foreign body response is to be minimized, for example on an housing of a pacemaker or defibrillator.

Finally, although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A medical electrical lead comprising:
a lead body, the lead body having a first conductor and an insulative sleeve positioned over the first conductor; and
an electrode assembly disposed at the distal end of the lead body; and
a rigid fixation mechanism disposed at the distal end of the lead body, the rigid fixation mechanism having an outer surface, the outer surface having at least one groove, the groove having a depth between approximately 0.1 to 30 microns, a width between approximately 0.1 to 30 microns.

2. A lead in accordance with claim 1 further comprising a series of grooves, each groove spaced apart from every other groove by a distance of between approximately 0.1 to 30 microns.

3. A lead in accordance with claim 2 wherein each groove is spaced apart from every other groove by a distance of between approximately 0.1 and 3 microns.

4. A lead in accordance with claim 1 wherein the groove is elongated.

5. A lead in accordance with claim 1 wherein the groove has a first side, and a bottom side, the first side meeting the bottom side at approximately a ninety degree angle.

6. A lead in accordance with claim 1 wherein the groove has a depth of approximately one micron and a width of approximately one micron.

7. A lead in accordance with claim 1 wherein the outer surface has a series of grooves, each groove is approximately parallel to an axis of the rigid fixation mechanism.

8. A lead in accordance with claim 1 wherein the outer surface has a series of grooves, each groove is parallel to any other groove.

9. A lead in accordance with claim 1 wherein the fixation mechanism is a helix.

10. A lead in accordance with claim 1 wherein the first conductor is coiled.

11. A lead in accordance with claim 1 further comprising a connector assembly positioned on a proximal end of the lead body.

12. A medical electrical lead comprising:
a lead body, the lead body having a first conductor and an insulative sleeve positioned over the first conductor; and
an electrode assembly disposed at the distal end of the lead body; and
a rigid helix disposed at the distal end of the lead body, the rigid helix having an outer surface, the outer surface having a series of longitudinal grooves, the grooves having a depth between approximately 0.1 to 30 microns, a width between approximately 0.1 to 30 microns.

13. A lead in accordance with claim 12 wherein each groove is spaced apart from every other groove by a distance of between approximately 0.1 to 30 microns.

14. A lead in accordance with claim 13 wherein the grooves have a depth between approximately 0.1 and 3 microns and the grooves having a width between approximately 0.1 and 3 microns.

15. A lead in accordance with claim 12 wherein at least one groove has a first side, and a bottom side, the first side meeting the bottom side at approximately a ninety degree angle.

16. A lead in accordance with claim 12 wherein each groove has a depth of approximately one micron and a width of approximately one micron.

17. A lead in accordance with claim 12 wherein each groove is approximately parallel to an axis of the rigid helix.

18. A medical electrical lead comprising:
a lead body, the lead body having a first conductor and an insulative sleeve positioned over the first conductor; and
an electrode assembly disposed at the distal end of the lead body; and a rigid helix disposed at the distal end of the lead body, the rigid helix having a treated surface, the treated surface having means for limiting the activation of macrophages wherein the treated surface comprises a series of grooves, the grooves having a depth between approximately 0.1 to 30 microns, a width between approximately 0.1 to 30 microns.

19. A lead in accordance with claim 18 wherein the grooves are longitudinal.

20. A lead in accordance with claim 18 wherein each groove in the series of grooves is spaced apart from every other groove by a distance of between approximately 0.1 to 30 microns.

21. A lead in accordance with claim 18 further comprising means for permitting the rigid helix to repeatedly extend from and retract into the distal end of the lead body.

* * * * *